US00PP31350P3

(12) United States Plant Patent
van Zoest

(10) Patent No.: US PP31,350 P3
(45) Date of Patent: Jan. 14, 2020

(54) ***CLEMATIS* PLANT NAMED 'ZO08171'**

(50) Latin Name: ***Clematis* hybrid**
Varietal Denomination: Zo08171

(71) Applicant: Jan van Zoest, Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 15/998,141

(22) Filed: Jul. 9, 2018

(65) Prior Publication Data

US 2019/0246539 P1 Aug. 8, 2019

(30) Foreign Application Priority Data

Feb. 8, 2018 (QZ) ..... PBR 20180435

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
See application file for complete search history.

*Primary Examiner* — Susan McCormick Ewoldt
(74) *Attorney, Agent, or Firm* — Penny J. Aguirre

(57) ABSTRACT

A new cultivar of hybrid *Clematis*, 'Zo08171', that is characterized by its free flowering habit as a nursery plant, its terminal and axillary flowers on young shoots, and its tulip-shaped flowers with a flower coloration that is unique for this shape of flower; tepals are violet with purple centers on the inner surface and dark red-purple with a violet margin on the outer surface.

2 Drawing Sheets

Botanical classification: *Clematis* hybrid.
Variety denomination: 'Zo08171'.

BACKGROUND OF THE INVENTION

The present invention relates to a new and distinct cultivar of *Clematis* of hybrid origin and will be referred to hereafter by its cultivar name 'Zo08171'.

*Clematis* 'Zo08171' is a climbing vine grown for use as a landscape plant.

*Clematis* 'Zo08171' was derived from an ongoing breeding program by the Inventor at his nursery in Boskoop, The Netherlands. The goal of the selection was to select a new cultivar of *Clematis* with tulip-shaped flowers with unique flower coloration. 'Zo08171' was selected in 2008 and arose from a controlled cross made in 2006 between unnamed and unpatented plants from his breeding program; the female parent designated as No. 19960253 and the male parent designated as No. 19970052.

Asexual propagation of the new cultivar was first accomplished by softwood stem cuttings under the direction of the Inventor in Boskoop, The Netherlands in 2008. Asexual propagation by softwood stem cutting has determined that the characteristics of the new cultivar are stable and are reproduced true to type in successive generations.

STATEMENT DESIGNATING A GRACE PERIOD UNDER 102(B)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventor; including but not limited to disclosures on websites by J Van Zoest, Thorncroft *clematis*, rhs, Crocus, Waitrosegarden, and Esveld.

SUMMARY OF THE INVENTION

The following traits have been repeatedly observed and represent the characteristics of the new cultivar. These attributes in combination distinguish *Clematis* 'Zo08171' as a unique cultivar of *Clematis*.

1. 'Zo08171' exhibits a free flowering habit as a nursery plant.
2. 'Zo08171' exhibits terminal and axillary flowers on young shoots.
3. 'Zo08171' exhibits tulip-shaped flowers with a flower coloration that is unique for this shape of flower; tepals are violet with purple centers on the inner surface and dark red-purple with a violet margin on the outer surface.

The female parent of 'Zo08171' differs from 'Zo08171' in having flowers that are larger, help upright, and are more spreading with flowers present on old wood and new shoots. The male parent of 'Zo08171' differs 'Zo08171' in having smaller flowers that are nodding and more bell-shaped. 'Zo08171' can be most closely compared to the *Clematis* cultivars 'Princess Diana' (not patented) and 'Zomibel' (not patented). Both are similar to 'Zo08171' in having tulip-shaped flower. 'Princess Diana' differs from 'Zo08171' in having flowers that are held nearly upright with tepals that are primarily red-purple in color and in having stamen filaments with a glabrous surface. 'Zomibel' differs from 'Zo08171' flowers that or nearly upright with tepals that are primarily pale purple in color, and in having stamen connectives with elongated hairy tips.

BRIEF DESCRIPTION OF THE DRAWINGS

The accompanying colored photographs illustrate the overall appearance and distinct characteristics of the new *Clematis*. The photographs were taken of a two-year-old plant as grown outdoors in a 2-Liter rose container in Boskoop, The Netherlands.

The photograph in FIG. 1 provides a view of 'Zo08171' in bloom.

Figure 1:
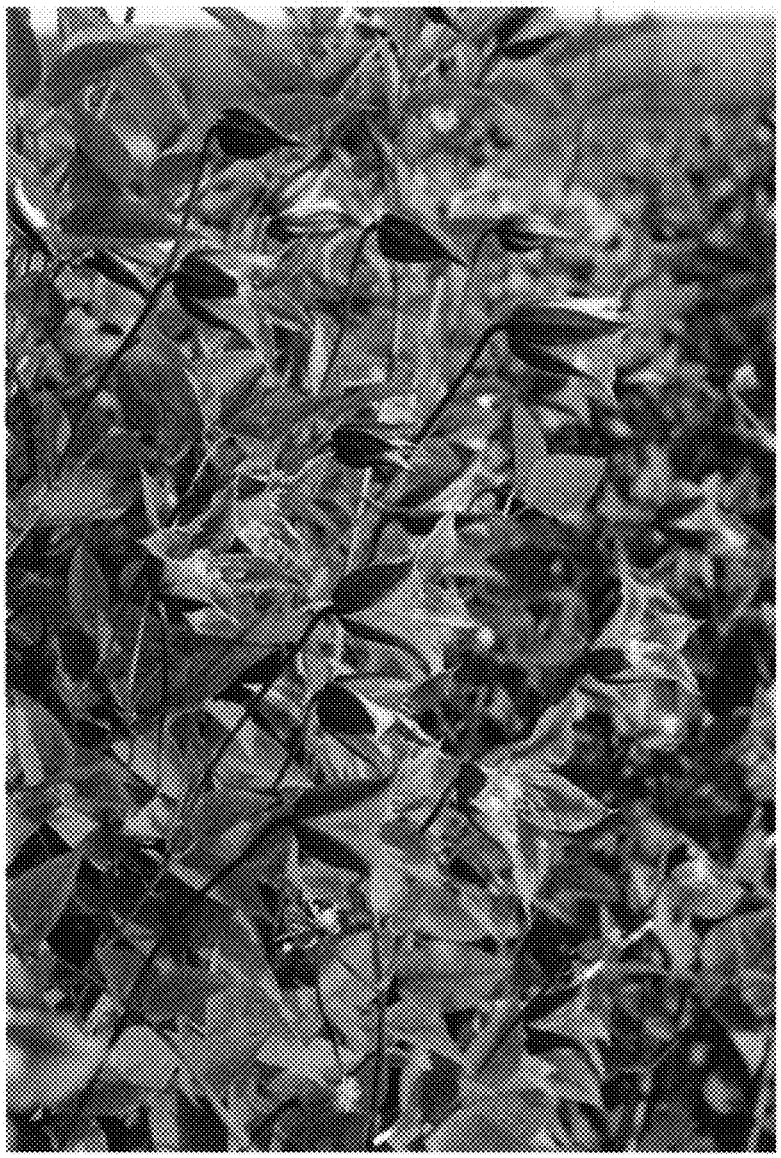
Figure 2:
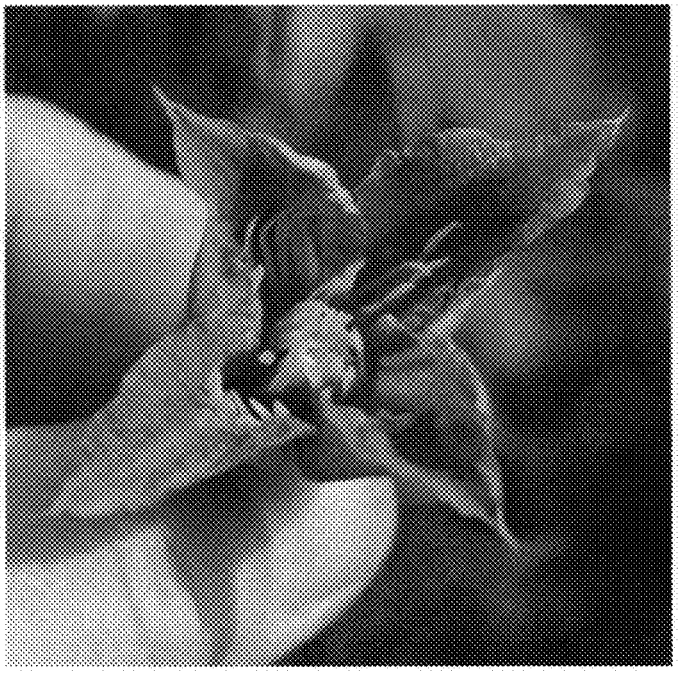

The photograph in FIG. 2 provides a close-up view of the inner surface of the flowers of 'Zo08171'.

Figure 3:
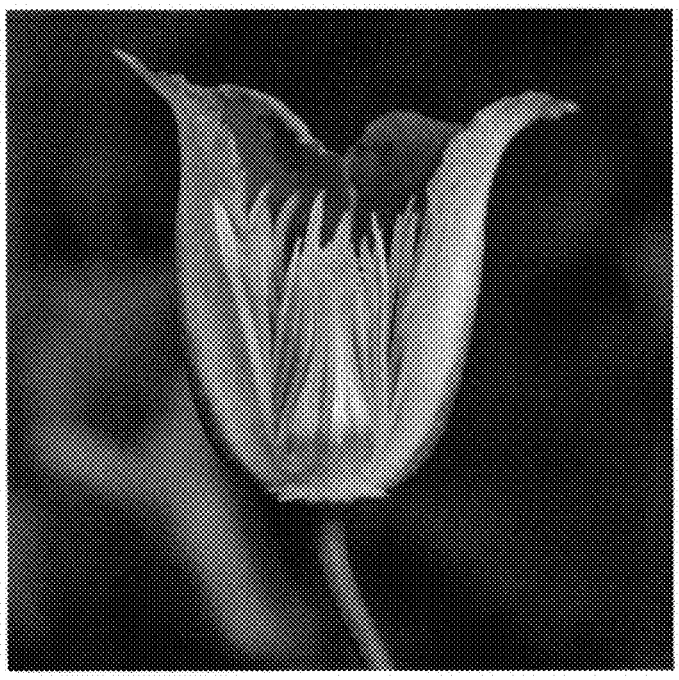

The photograph in FIG. 3 provides a close-up view of a cross section of a s flower of 'Zo08171'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of two-year-old plants as grown outdoors in 2-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2001 Colour Chart of The Royal Horticultural Society, London, England, except where general color terms of ordinary dictionary significance are used.

General description:

*Botanical classification.*—*Clematis* 'Zo08171'.
*Blooming period.*—Late spring to early Autumn.
*Plant type.*—Deciduous woody vine, blooms on new shoots only.
*Plant habit.*—Climber.
*Height and spread.*—Three-year-old plant reaches 2 to 3 m in height and 20 cm in spread at the base.
*Cold hardiness.*—At least to U.S.D.A. Zone 6.
*Culture.*—Moist but well-drained soils in full sun with the roots shaded.
*Diseases and pests.*—Susceptibility to powdery mildew caused by *Erysiphe polygoni* is unknown, no pest problems have been observed.
*Root description.*—Fleshy.
*Propagation.*—Softwood cuttings.
*Root initiation.*—Roots develop in 5 weeks in summer under greenhouse conditions.
*Time required for root development.*—75 to 90 days to fully develop in a 7-cm container from a 5-cm cutting.
*Growth rate.*—Moderately vigorous.

Stem description:

*Shape.*—Round with 6 ribbed angles.
*Stem color.*—144B, flushed with 59C and becoming N167D.
*Stem size.*—Up to 3 m in length, an average of 3 mm in width.
*Stem surface.*—Sparsely hairy.
*Internode length.*—Up to 20 cm.
*Branching.*—Primarily from the base, also starting below the flowering part of the stem.

Foliage description:

*Leaf arrangement.*—Opposite.
*Leaf division.*—Pinnate.
*Leaf size.*—Up to 25 cm in length and 20 cm in width.
*Leaf attachment.*—Petiolate.
*Leaf fragrance.*—Slight Honey-like fragrance when crushed.
*Leaflet shape.*—Ovate.
*Leaflet size.*—Lower leaflets; up to 7 cm in length and 5 cm in width, terminal leaflets; up to 2.5 cm in length and 1.5 cm in width.
*Leaflet base.*—Subcordate.
*Leaflet apex.*—Acuminate.
*Leaflet venation.*—Upper surface; slightly reticulate, lower surface; reticulate, both surfaces are 143C in color.
*Leaflet quantity.*—5, occasionally 7.
*Leaflet margin.*—Entire, lower leaflets sometimes lobed to cleft.
*Leaflet surface.*—Upper surface; glabrous, lower surface; glabrous but sparsely hairy with main veins.
*Leaf color.*—Upper surface; 137B, lower surface; 147B.
*Petioles.*—Up to 6 cm in length, 2 mm in diameter, 146B in color, round in shape, surface sparsely hairy, aspect typically straight and sometimes curling.
*Petiolules.*—Terminal leaflet up to 1 cm in length, side leaflets up to 3 cm in length, 1 mm in width, round in shape, surface sparsely hairy, 146B in color, straight to strongly curly.

Inflorescence description:

*Inflorescence type.*—Solitary or a 3 to 7-flowered dichasial cyme.
*Inflorescence arrangement.*—Terminal and axillary on young shoots.
*Peduncles.*—Up to 15 cm in length, 2 mm in width, 143B in color flushed with 59C on upper surface, round in shape, surface sparsely hairy.
*Pedicels.*—Up to 13 cm in length, 2 mm in diameter, 143C in color, round in shape, surface sparsely hair.
*Flower buds.*—Nodding, ovate in shape, up to 4 cm in length and 1.5 cm in diameter, 144B, flushed with 59C in color, surface sparsely hairy.
*Flower fragrance.*—None.
*Lastingness of the flowers.*—Individual flowers last up to 5 days.
*Flower quantity.*—Up to 50 to 100 flowers on a 3-year-old plant.
*Flower type.*—Campanulate, tulip-like.
*Flower aspect.*—Horizontal.
*Flower shape.*—Tulip-shaped.
*Flower size.*—4 to 6 cm in diameter and 4 to 5 cm in depth.
*Flower sex.*—Bisexual.
*Bracts.*—Simple, ovate in shape, up to 7 cm in length and 5 cm in width, acuminate apex, entire margin, base is cordate in shape, venation is reticulate, surfaces covered with sparse hairs and glabrous, color; upper surface 137B, veins 137D, lower surface 147B, veins 147C.
*Tepal number.*—4, occasionally 6 during first bloom.
*Tepal shape.*—Rhomboidal.
*Tepal aspect.*—Lower half of margins curl inwards.
*Tepal apex.*—Acuminate.
*Tepal base.*—Cuneate.
*Tepal margin.*—Crinkled.

*Tepal surface*.—Upper surface; glabrous, lower surface; margin slightly villous, middle section is sparsely hairy.

*Tepal color*.—Upper surface; N89B with a tint of N66, lower half 93B, 4 mm base 155A, lower surface; 64A with tint of N66, margin N82C.

*Tepal size*.—Up to 5 cm in length and an average of 2 cm in width.

Reproductive organs:

*Gynoecium*.—Average of 60 to 70 pistils, up to 1.5 cm in length, ovary; 144C in color and silvery and hairy, style; 18D in color, hairy, stigma; straight to slightly curled in aspect, 155B in color, glabrous.

*Androecium*.—Filaments; up to 2 cm in length, 0.5 mm in width and linear to filiform in shape, surface is glabrous with upper half short hairy, 149D with 91C at the base in color, anthers; 4 mm in length, 0.8 mm in width, linear in shape, and 4D in color, pollen; 155D in color and moderate in quantity, connective; 1.5 mm in length, straight in aspect, apex obtuse, surface is glabrous and 4B in color.

*Seed*.—None, sterile.

It is claimed:

1. A new and distinct cultivar of *Clematis* plant named 'Zo08171' as herein illustrated and described.

* * * * *